(12) United States Patent
Landau et al.

(10) Patent No.: US 6,752,781 B2
(45) Date of Patent: Jun. 22, 2004

(54) DURABLE HYPODERMIC JET INJECTOR APPARATUS AND METHOD

(76) Inventors: Sergio Landau, 49 South Peak, Laguna Nigel, CA (US) 92692; Daniel Williamson, 23785 SE. Brittany La., Sherwood, OR (US) 97140

( * ) Notice: Subject to any disclaimer, the term of this patent is extended or adjusted under 35 U.S.C. 154(b) by 0 days.

(21) Appl. No.: 10/057,052

(22) Filed: Jan. 25, 2002

(65) Prior Publication Data

US 2002/0188250 A1 Dec. 12, 2002

Related U.S. Application Data

(63) Continuation-in-part of application No. 09/877,911, filed on Jun. 8, 2001.

(51) Int. Cl.[7] .............................................. A61M 5/30
(52) U.S. Cl. ........................... 604/70; 604/68; 604/71; 604/140; 604/141; 604/181; 604/209
(58) Field of Search ............................ 604/68–72, 136, 604/140–145, 181–187, 207–211, 246

(56) References Cited

U.S. PATENT DOCUMENTS

| | | | | |
|---|---|---|---|---|
| 4,596,556 A | * | 6/1986 | Morrow et al. | 604/70 |
| 5,453,096 A | * | 9/1995 | Lataix | 604/246 |
| 5,503,627 A | * | 4/1996 | McKinnon et al. | 604/72 |
| 5,599,302 A | * | 2/1997 | Lilley et al. | 604/68 |
| 5,730,723 A | * | 3/1998 | Castellano et al. | 604/68 |
| 5,891,085 A | * | 4/1999 | Lilley et al. | 604/68 |
| 6,063,053 A | * | 5/2000 | Castellano et al. | 604/68 |
| 6,080,130 A | * | 6/2000 | Castellano | 604/68 |
| 6,096,002 A | * | 8/2000 | Landau | 604/68 |
| 6,156,008 A | * | 12/2000 | Castellano | 604/116 |
| 6,264,629 B1 | * | 7/2001 | Landau | 604/68 |

* cited by examiner

*Primary Examiner*—Gregory L. Huson
*Assistant Examiner*—Amanda Flynn

(57) ABSTRACT

A gas-powered, durable, needle-less hypodermic jet injection device (10, 210) includes a hand-held injector (12, 212) which receives into an injection cylinder a volume of liquid medication to be injected in the form of a high velocity jet capable of penetrating the skin without the use of a hypodermic needle. The injection device provides an injection orifice, and an injection piston. Forceful movement of the injection piston causes a high velocity injection jet of liquid medication to be expelled from the injection cylinder via the injection orifice. The injection device includes features which improve its usability, particularly for users with hands that are possibly weak, feeble, or arthritic, for example; and also includes additional features which improve manufacturability, durability, and cost effectiveness of the device.

14 Claims, 7 Drawing Sheets

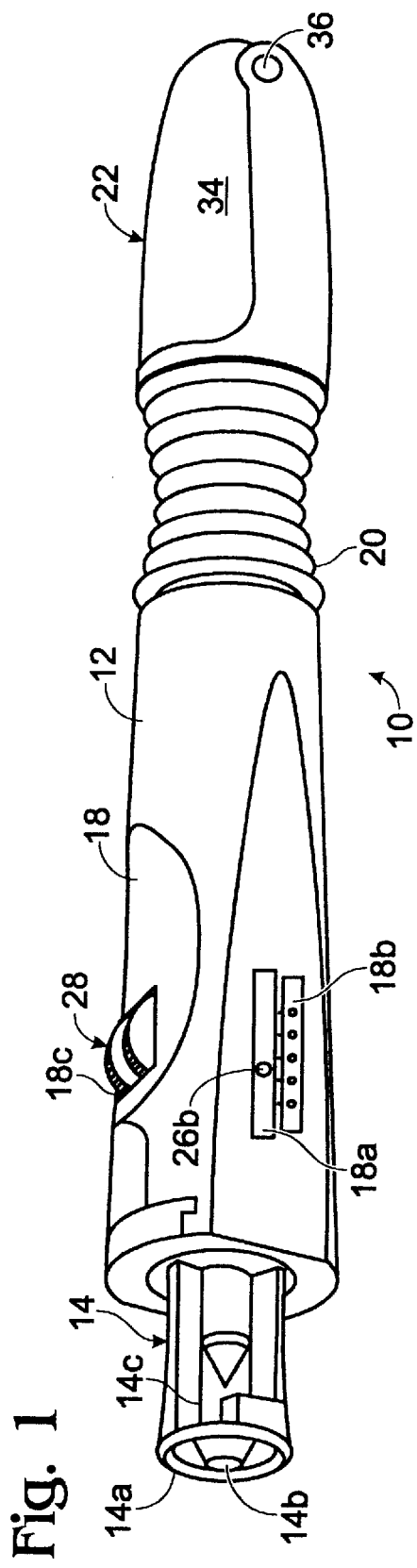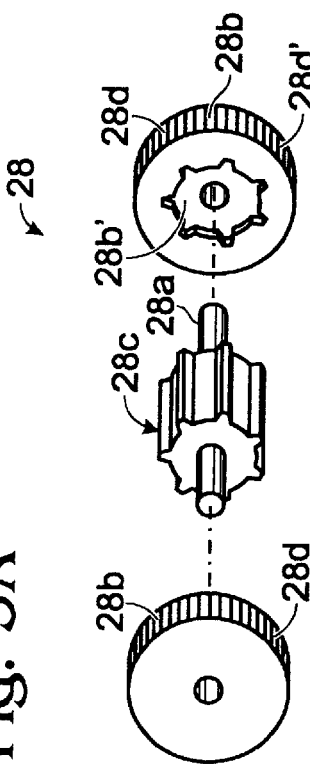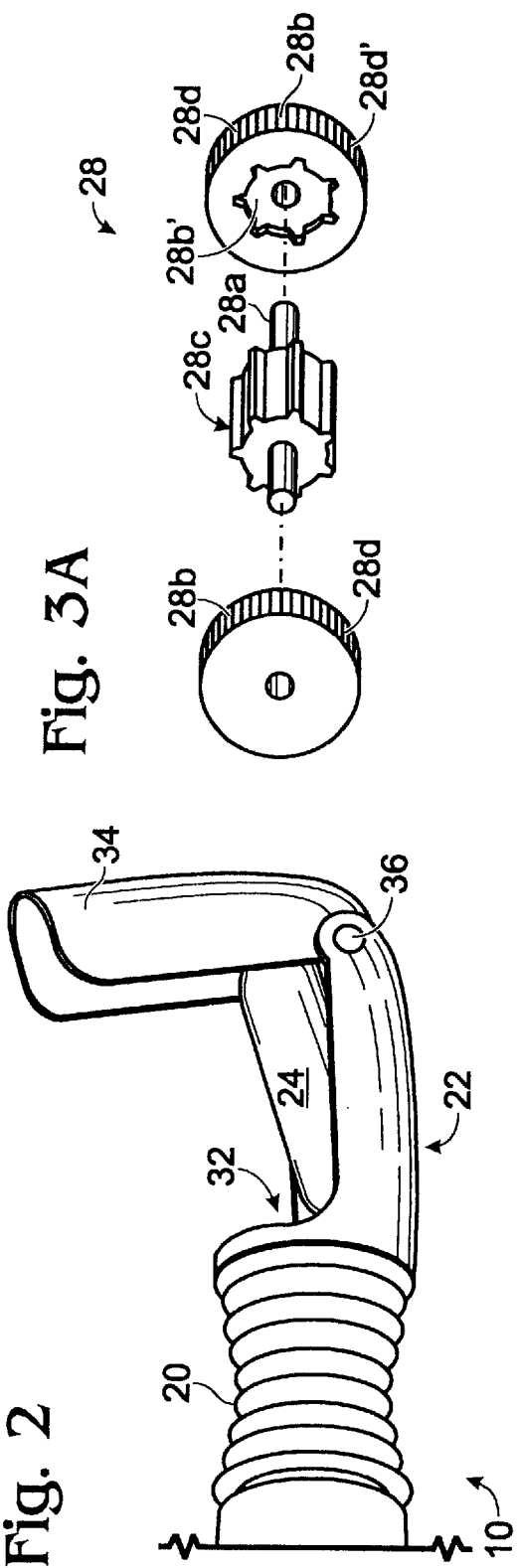

DURABLE HYPODERMIC JET INJECTOR APPARATUS AND METHOD

CROSS REFERENCE TO RELATED APPLICATION

This application is a Continuation-in-Part of U.S. patent application Ser. No. 09/877,911, filed Jun. 8, 2001, and the content of which is incorporated herein by reference to the extent necessary for a complete and enabling disclosure of the present invention.

BACKGROUND OF THE INVENTION

1. Field of the Invention

The present invention relates generally to a durable, multiple-use needle-less (or needle-free) hypodermic jet injection device, and to methods of its making, operation, and use. More particularly, this present invention relates to such a device and to such methods which provide improved facility for use by user, especially for a user whose hands my be feeble or arthritic, and also for improved manufacturability, and further for improved effectiveness of use and operation in effecting a needle free hypodermic jet injection.

2. Related Technology

Needle-less or needle-free hypodermic jet injection devices have been in commercial use for over 40 years. A number of these devices have used pressurized gas to power a hypodermic jet injection. The related technology includes a number of teachings for gas-powered injection devices, including: U.S. Pat. No. 4,596,556, issued Jun. 24, 1986 to J. Thomas Morrow, et al.; U.S. Pat. No. 4,913,699; issued Apr. 3, 1990 to James S. Parsons; and U.S. Pat. No. 5,730,723, issued Mar. 24, 1998, to Thomas P. Castellano, et al. WIPO publication WO 97/37705 also discloses a gas powered disposable needle-less hypodermic jet injector.

The Morrow, et. al. '556 patent is believed to teach a reusable hypodermic jet injection device in which a housing receives a shell or cartridge having a bore leading to a discharge aperture. Within the bore is received both a plunger sealingly engaging the bore, and a pressurized gas cylinder which rests against the plunger. The injection device includes a ram which has a penetrating tip confronting a penetrable wall section and seal of the gas cylinder, and a discharge mechanism for driving the ram through the penetrable wall section of the gas cylinder when a trigger device is released. Discharge of the pressurized gas from the cylinder drives the plunger to effect a jet injection, and also drives the seal of the gas cylinder to effect resetting of the discharge mechanism. The shell with its plunger, and spent gas cylinder, is discarded after an injection; and a new shell pre-filled with medication and with a new gas cylinder is used for each injection.

The Parsons '699 patent is believed to teach a single-use jet injector which is totally discarded after one use. This injector is believed to have a body with a pair of gas chambers separated by a breakable valve. One of the gas chambers contains a pressurized gas, while the other chamber is sealingly bounded by a piston which drives a plunger. The plunger sealingly bounds a chamber into which a dose of medication is loaded by the user before the injection. This medication dose chamber leads to an injection orifice so that when the valve is broken, the piston and plunger are moved by pressurized gas communicated to the second chamber, and the plunger drives the medication forcefully out of the injection orifice to form an injection jet. After a single use, the device is discarded.

The Castellano '723 patent, which was issued in 1998 and which does not cite the earlier Parsons '699 patent, is believed to teach substantially the same subject matter as Parsons et al.

WIPO publication WO 97/37705 published pursuant to a Patent Cooperation Treaty (PCT) application for joint inventors Terence Weston and Pixey Thornlea, is believed to disclose a disposable hypodermic jet injector in which the device is powered by a gas pressure spring of the type common in the tool and die art as a substitute for the conventional metal spring-powered ejector pin. In the Weston device, the ram of the gas pressure spring is held in a contracted position by a trigger mechanism. When the trigger mechanism is released, the gas pressure spring is supposed to expand and drive a piston sealingly received in a bore and leading to a fine-dimension orifice in order to produce a jet hypodermic injection from liquid held in the bore ahead of the piston.

The Weston device is thought to have several deficiencies: such as difficult and costly manufacturing and sterilization processes, because pressurized gas and a drug dose need to be contained in the same package; and including a possible inability to endure long-term storage while still retaining the gas pressure in the gas spring to power an injection, and also maintaining the medication integrity. In other words, the gas pressure spring of the Weston device contains only a small quantity of gas, and depends upon the sealing relationship of the ram of this spring with a cylinder within which the ram is movably and sealingly received in order to retain this gas pressure. Even a small amount of gas leakage over time will be enough to render this injector inoperative.

SUMMARY OF THE INVENTION

In view of the above, it is desirable and is an object for this invention to provide a needle-less jet injection device which reduces the severity of or avoids one or more of the limitations of the conventional technology.

Thus, it is an object of this invention to provide a durable, needle-free gas-powered hypodermic jet injector providing for greater and improved ease in loading and operation for a user, particular for a user whose hands may be feeble or arthritic. In this respect, the present invention provides a more easily usable mechanism for drawing into and measuring a dose of medication within the injector device.

Further, this present invention provides an improved facility for a user to load and unload a pressurized gas capsule into and from the device.

Still further, a unique valving mechanism of the injector is especially configured for improved manufacturing, and for a concomitant improved reliability and durability in use of the device.

Further, the present invention improves the effectiveness of the formation of a high velocity hypodermic injection jet utilizing a source of pressurized gas that is controllably released from a pressurized gas capsule. That is, the present device avoids the shortcoming of allowing the pressurized gas to expand to a greater volume and lower pressure before significant energy from the gas is transferred to a dose of liquid medication in order to force the medication through a fine dimension orifice to form a hypodermic injection jet. Because the pressurized gas is utilized at the smallest practicable volume and highest practicable pressure level, the essential energy transfer from the pressurized gas to the liquid medication is effected most expediently and most effectively to provide the greatest possible velocity and energy level in the hypodermic injection jet.

Accordingly, an embodiment of the present invention provides a jet injection device comprising: a device body having a forward end; an injection cylinder at the forward end of the device body, and the injection cylinder having a cylinder bore in which an injection piston is sealingly movable to cooperatively define a variable-volume chamber for holding a dose of liquid medication; the injection cylinder defining a fine-dimension injection orifice in liquid flow communication with the variable-volume chamber to receive and discharge liquid medication as a forceful high velocity jet upon forceful movement of the injection piston in the cylinder; a power source in the device body for forcefully moving the injection piston in the cylinder in response to communication of gas pressure to a gas pressure piston; the power source including a source of pressurized gas for selective communication with the gas pressure piston; a trigger assembly for selectively effecting communication of pressurized gas from the source to the gas pressure piston; and a lost motion preventing mechanism selectively drivingly connecting the gas pressure piston to the injection piston.

According to a further aspect this invention provides: a method of providing a gas powered hypodermic jet injection device, the method comprising steps of: providing a device body having a forward end; providing an injection cylinder at the forward end of the device body, disposing sealingly in the injection cylinder an injection piston to cooperatively define a variable-volume chamber for holding a dose of liquid medication; providing the injection cylinder with a fine-dimension injection orifice in liquid flow communication with the variable-volume chamber, and utilizing the injection orifice to receive and discharge liquid medication as a forceful high velocity jet upon forceful movement of the injection piston in the injection cylinder; providing a power source in the device body for forcefully moving the injection piston in the cylinder in response to communication of gas pressure to a gas pressure piston; providing for the power source to include a source of pressurized gas for selective communication with the gas pressure piston; providing a trigger assembly for selectively effecting communication of pressurized gas from the source to the gas pressure piston; and configuring the device body to define an axially elongate recess opening along a side thereof, providing a door member in a first position closing the recess and the door member opening to a second position to reveal the recess and a penetrator member disposed within the recess; providing for the recess to be sized and configured to accept a pressurized gas capsule including a penetrable diaphragm portion and an end surface opposite to the penetrable diaphragm portion; including on the door member a camming surface engaging the end surface, and in response to closing of the door member from the second position to the first position utilizing the camming surface to move the pressurized gas capsule fully into the recess and to be impaled at the penetrable diaphragm portion upon the penetrator member.

Additional objects and advantages of this invention will appear from a reading of the following detailed description of two exemplary preferred embodiments of the invention, taken in conjunction with the appended drawing Figures, in which the same reference numeral is used throughout the several views to indicate the same feature, or features which are analogous in structure or function.

BRIEF DESCRIPTION OF THE DRAWING FIGURES

FIG. 1 provides an exterior perspective view of a durable, needle-less hypodermic jet injector device embodying the present invention;

FIG. 2 is a fragmentary perspective view taken from an aspect different than that of FIG. 1, and showing a loading door of the device opened and a gas pressure cartridge of the device in the process of insertion or withdrawal from the device.

FIG. 3 provides a side elevation view, partially in cross section, of the jet injection device seen in FIGS. 1 and 2, and is shown with the loading door open and the pressurized gas cartridge in the position seen in FIG. 2;

Figure 3:
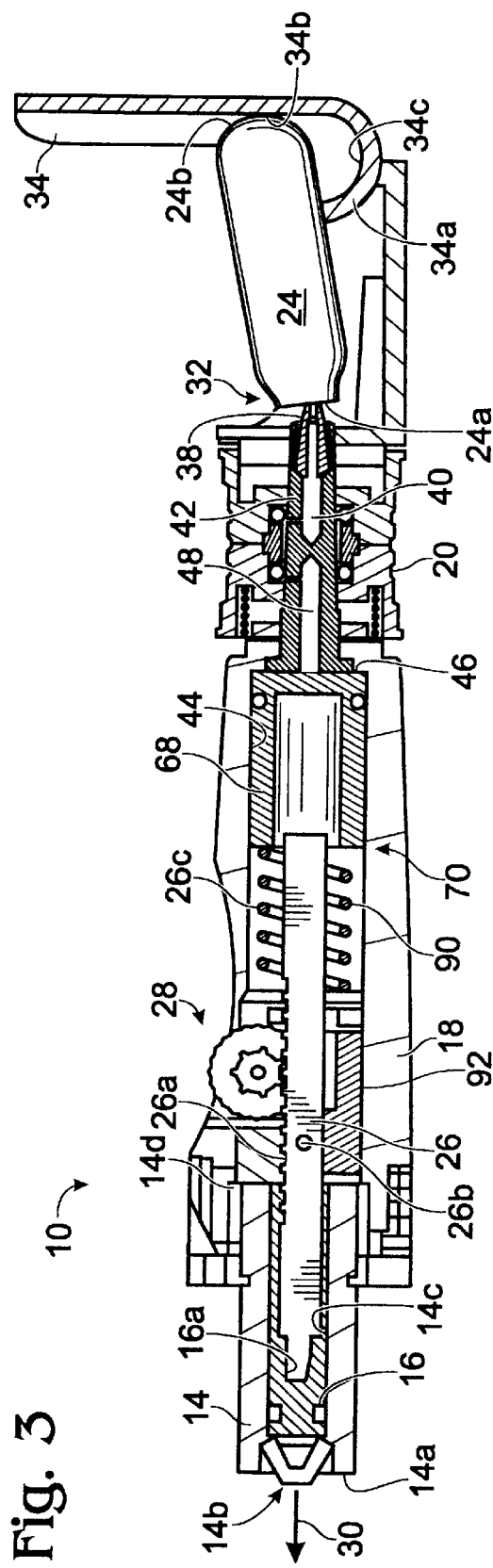
FIG. 3a is a fragmentary exploded perspective view of a portion of the device.
Figure 4:
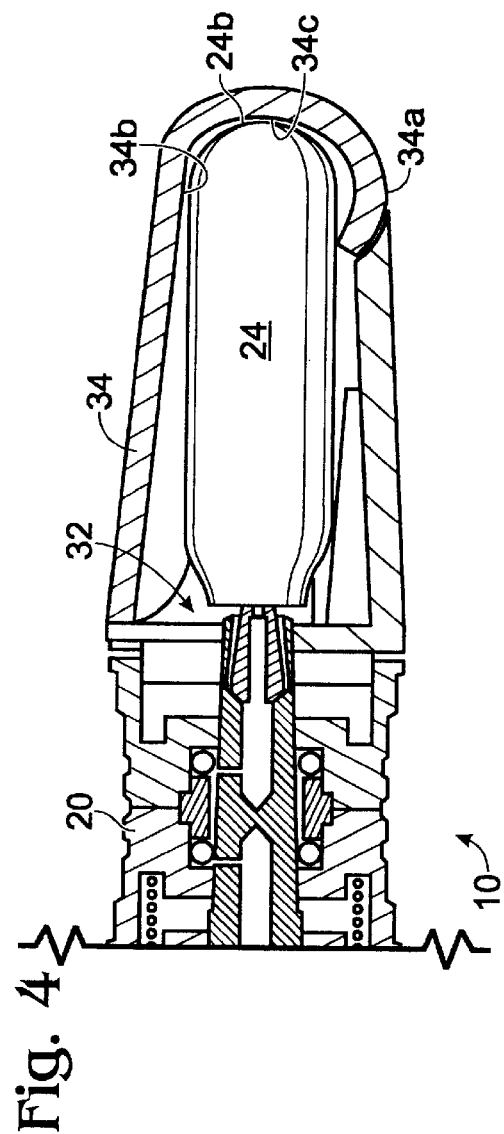
FIG. 4 is a fragmentary cross sectional similar to a portion of FIG. 3, but showing the loading door closed and the pressurized gas cartridge in an operative position preparatory to the effecting of a hypodermic jet injection using the device.
Figure 7:
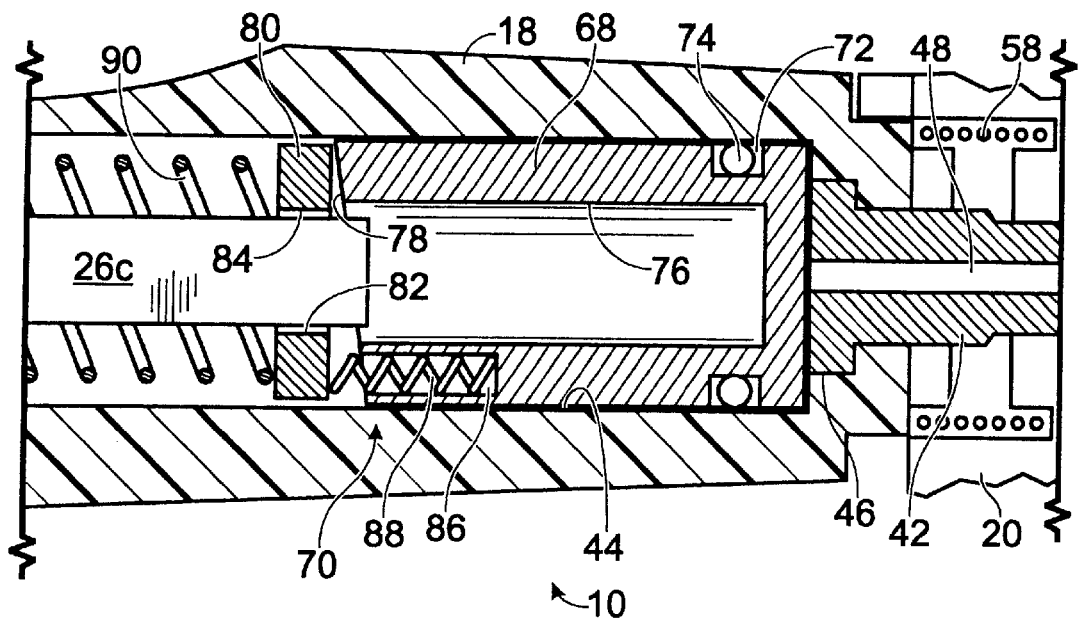
Figure 8:
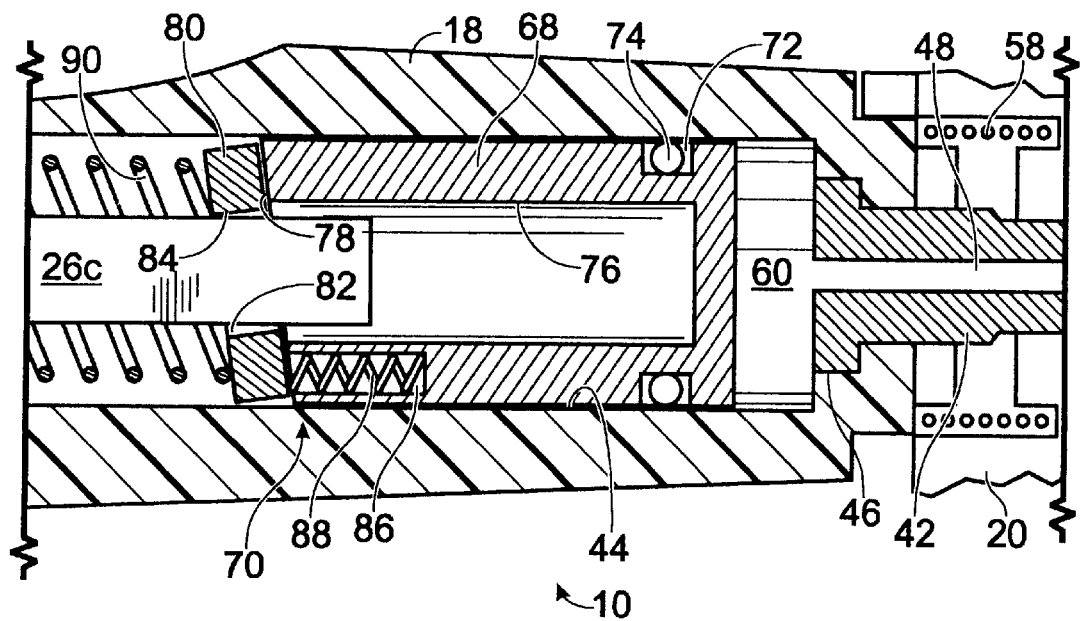
Figure 9:
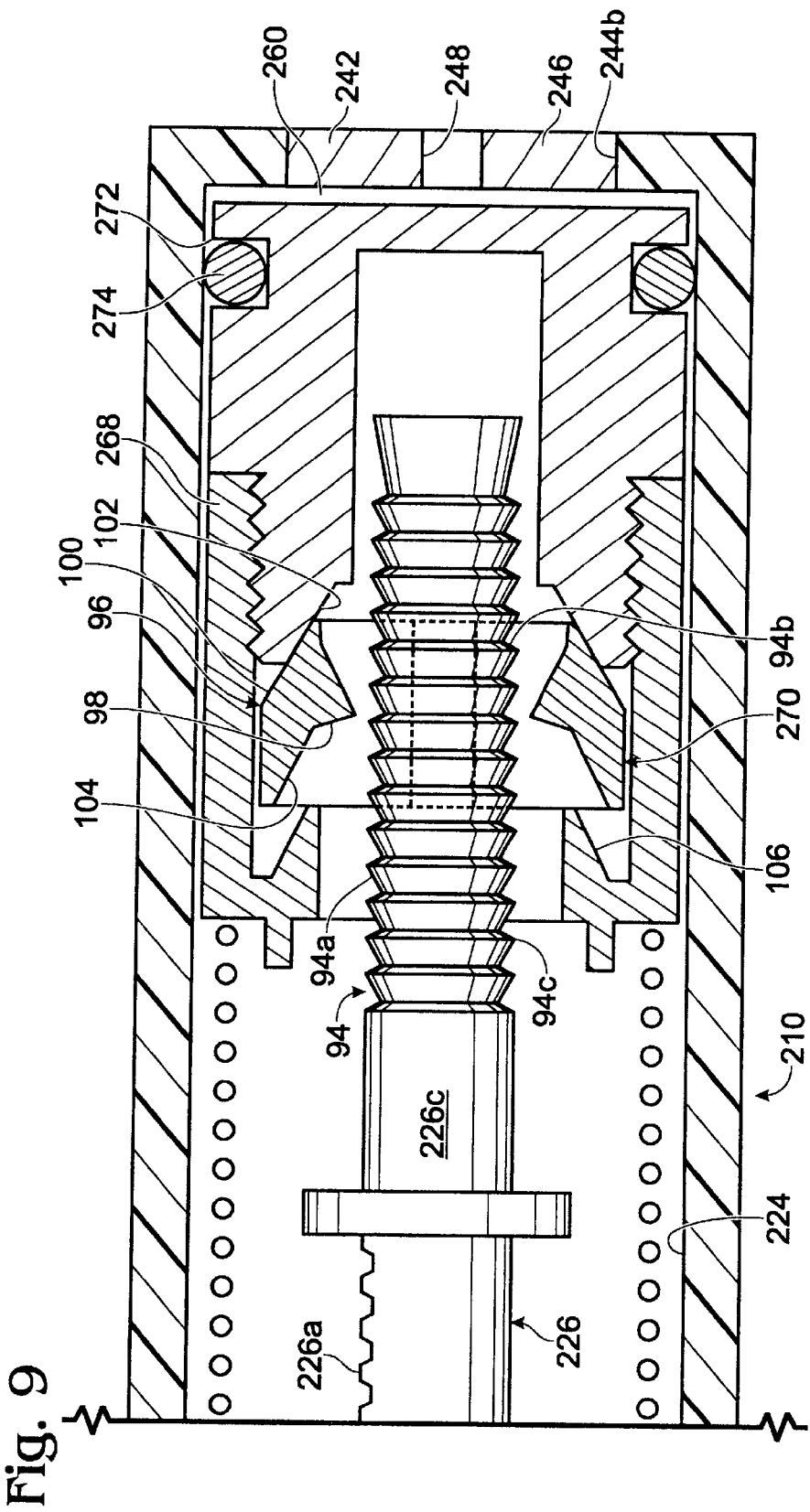
Figure 10:
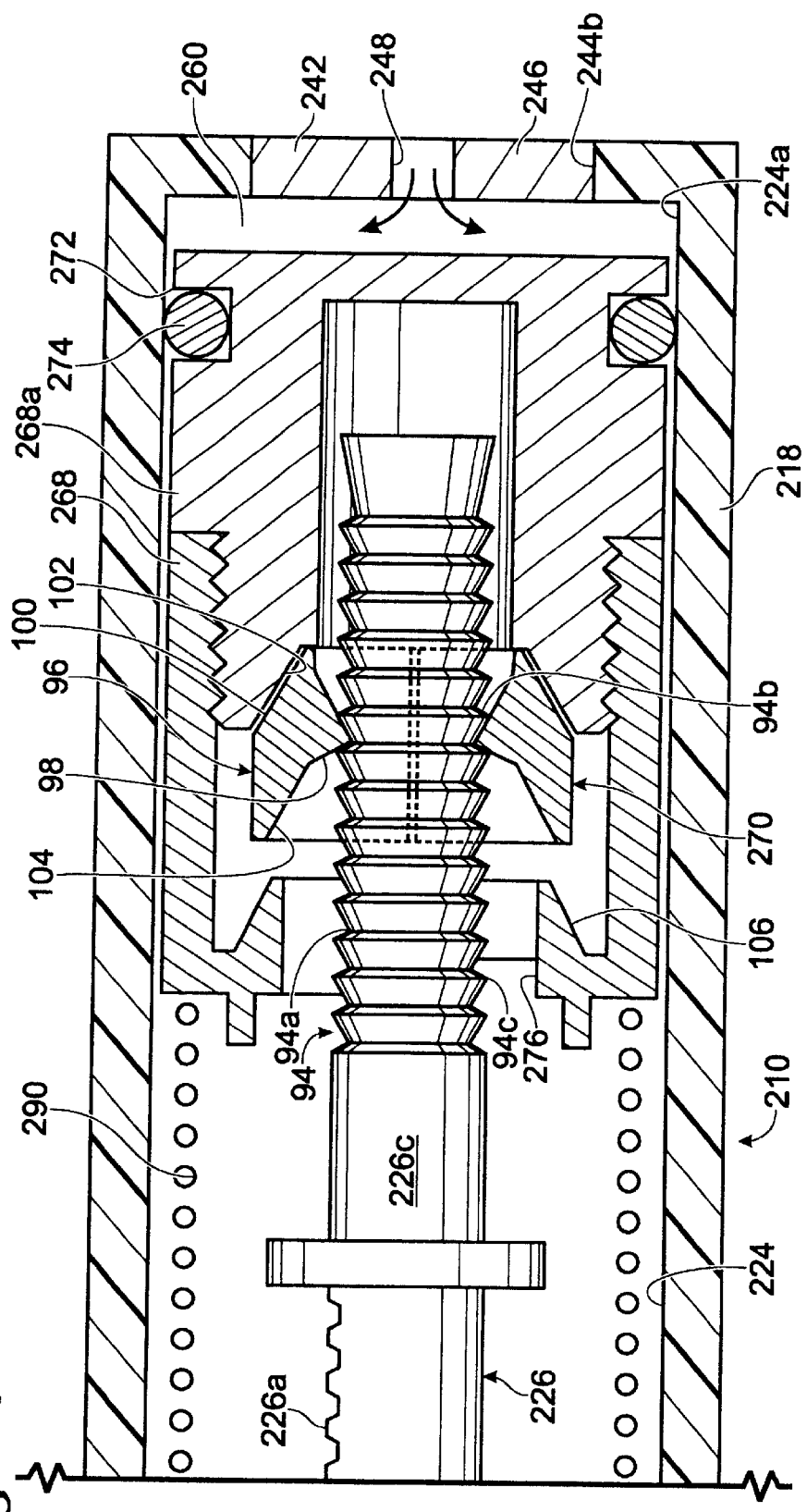
Figure 11:
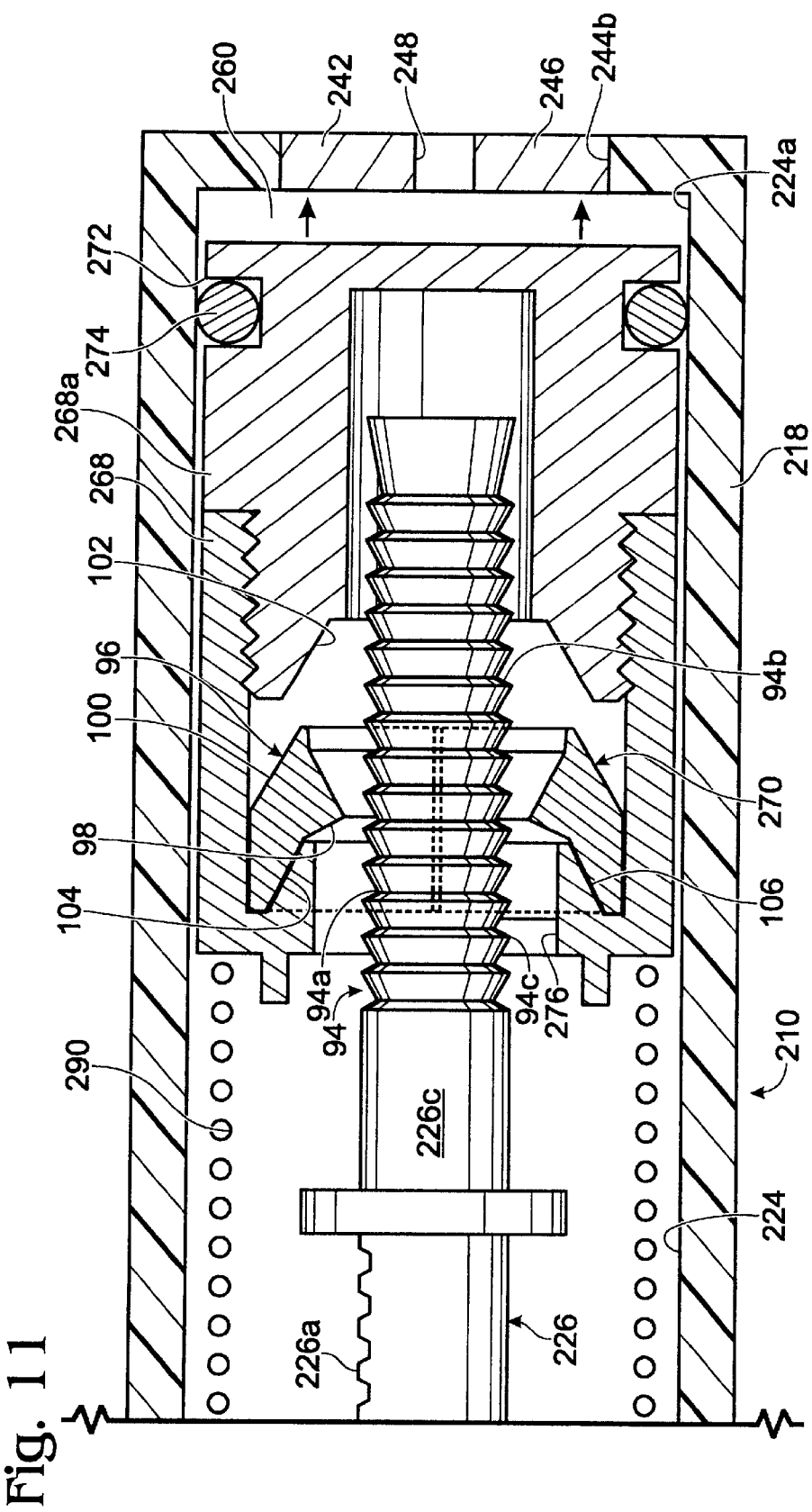

FIGS. 7 and 8 are also each enlarged fragmentary cross sectional views similar to enlarged portions of FIGS. 3 and 4, but showing a gas piston portion of the device in respective operative positions, with the position of FIG. 7 being preparatory to a hypodermic jet injection, and the position of FIG. 8 being during such a jet injection; and FIGS. 9, 10, and 11 are each enlarged fragmentary cross sectional views similar to enlarged portions of FIGS. 3 and 4, but showing equivalent portions of an alternative embodiment of the invention, in which a gas piston portion of the device is shown in respective operative positions, which are preparatory to (FIG. 9), during (FIG. 10), and subsequent to (FIG. 11) a hypodermic jet injection.

DETAILED DESCRIPTION OF EXEMPLARY PREFERRED EMBODIMENTS OF THE INVENTION

Overview of the Injection Device and its Use

Viewing FIGS. 1, 2, and 3 in conjunction with one another, a needle-free, hypodermic jet injection device 10 is illustrated. This device 10 includes a multi-piece body 12, including a removable injection cylinder member 14, having an injection piston 16 (best seen in FIG. 3) sealingly and movably received therein. A forward body section 18 of the device 10 carries a trigger sleeve 20, and an aft body section 22 receives a pressurized gas cartridge 24 (as is seen in FIG. 2). The injection piston 16 is removably attached to a reciprocable ram member 26 (also best seen in FIG. 3), which is reciprocable in the forward body section 18. The injection piston 16 defines a recess 16a (best seen in FIG. 3) for "snapping" onto an end fixture of the ram 26. It is to be understood that the injection cylinder 14 and injection piston 16 are capable of being used more than once on the same recipient to effect a hypodermic jet injection to that particular individual, but may be used only once if desired, and may be disposed of when the user is finished using a particular injection cylinder 14 and piston 16 (i.e., after only a single injection or after several injections to the same person). Thus, it is to be understood that both the injection piston 16 and injection cylinder 14 are usable more than once if desired, but are also removable from the device 10, so that they can be replaced with a new injection cylinder and new injection piston.

A user of the device 10 prepares the device to effect an injection by attaching a medicine vial (not shown in the drawing Figures) to the end of the injection cylinder 14, and utilizes a protruding thumb wheel assembly 28 (which is actually and preferably configured as a pair of thumb wheel portions side by side, viewing FIG. 1) on the body portion 18 to effect rearward movement of the ram 26 and injection piston 16. This rearward movement of the piston 16 within cylinder 14 causes medication to be drawn into the injection cylinder 14 via a fine dimension injection orifice (to be further identified below) which is defined at the front of this injection cylinder 14. It will be noted that the drug injection cylinder 14 has an end surface 14a at which is defined the fine-dimension injection orifice opening 14b (again viewing FIG. 3). The injection piston 16 is sealingly and movably received into a larger diameter bore 14c of the cylinder 14. And, the cylinder 14 includes a pair of radially outwardly extending and axially tapering latching lugs 14d which are captively and releasably captured within the body portion 18, and by which the cylinder 14 removably latches into the body portion 18. When the device 10 is used to effect a hypodermic jet injection, a high velocity jet of liquid medication issues from the orifice 14b (as is indicated by arrow 30 of FIG. 3).

To use the device 10, the user fills the injection cylinder with liquid medication, as was explained above, and then places a pressurized gas cartridge 24 into a recess 32 at the aft end of aft body section 22. In order to access the recess 32, the user swings open a pivoting door 34 which is pivoted between a pair of rearwardly projecting extensions 36 (only one of which is seen in FIGS. 1 and 2), of the housing 12. When the door 34 is opened, as is seen in FIGS. 2 and 3, the recess 32 is opened, and the pressurized gas cartridge 24 is inserted as is seen in FIGS. 2 and 3, with its penetrable end 24a disposed toward a penetrator member 38 carried by the handpiece assembly 12. As is seen in FIGS. 2 and 3, when the door 34 is opened fully, the pressurized gas cartridge 24 is disposed angularly (that is, at a slight angle with respect to axial alignment to the body 18) relative to the device 10.

The door 34 is then forcefully pivoted closed, to the position seen in FIGS. 1 and 4, which results in the pressurized gas cartridge 24 being pivoted into axial alignment with the body 18, and being forced slightly forwardly within the recess 32, and consequently results in the gas cartridge 24 being impaled upon the penetrator member 38, as is seen in FIG. 4. Penetration of the pressurized gas cartridge 24 by the penetrator member 38 (which is a tubular member) communicates pressurized gas through the penetrator member 38, and into the blind bore 40 of a stem member 42 (upon which the trigger sleeve 20 is movably and sealingly carried), and to a valved chamber (to be further explained) through which communication of pressurized gas is controlled by the relative position of trigger sleeve 20.

Subsequently, the end surface 14a is pressed against the skin of a patient or individual who is to receive the jet injection, and then the device 10 is triggered by forward movement of the trigger sleeve 20 so that the jet 30 issues out of orifice 14b and penetrates the patient's skin. Thus, the liquid medication enters the tissues of the patient without the use of a hypodermic needle.

After the injection is completed, the user may pivot the door 34 back to its position seen in FIG. 2 in order to remove the spent gas cartridge 24 from the device 10 in preparation for its next use. As will be seen, the door 34 has a feature which lifts the gas cartridge partially out of the recess 32 in response to opening of this door member, so that the user of the device 10 may easily remove the spent gas cartridge from the device 10.
Structure of the Device 10

Turning now to FIGS. 3 and 4 in conjunction with one another, FIG. 3 shows a longitudinal cross sectional view of the device 10 in a preparatory condition. That is, the pressurized gas cartridge 24 is disposed within recess 32, but is not yet penetrated. In this position of the gas cartridge, it is seen that the door 34 provides a reentrant terminal end portion 34a, which in the fully opened position of the door 34 provides a rest upon which is disposed the gas cartridge in a slightly angulated position relative to axial alignment with the body 18. Door 34 also provides a camming (or forcing) surface 34b, which slidably engages the aft end 24b of the gas cartridge. This door 34 also provides an arcuate recess 34c which will receive the aft end 24b of the gas cartridge 24 when the door 34 is fully closed, as will be further explained.

In FIG. 4 the device 10 is fragmentarily shown in longitudinal cross section preparatory to administering an injection, and after the door 34 has been forced to its fully closed potion, forcing the gas cartridge 24 onto the penetrator 38. As is seen in FIG. 4, the aft end 24b of the gas cartridge now resides in recess 34c of the door, after having slid forward along camming surface 34b. In this closed position of the door 34, the reentrant end portion 34a services to close an opposite portion of the recess between the two projections 36, as is best seen in FIG. 2. However, as seen in FIG. 3, it will be understood that after the pressurized gas cartridge 24 is spent, and upon the full reopening of door 34, the terminal end portion 34a of this door tips the gas cartridge out of engagement with the penetrator 38 and slightly out of the recess 24, so that the gas cartridge is thereafter easily removed from the device 10.

Turning to FIG. 3 and fragmentary exploded view 3a, it is seen that the thumbwheel assembly 28 is in fact composed of several component parts assembled with and rotational in the housing portion 18 on an axle shaft 28a. The thumbwheel assembly 28 includes two thumbwheel members 28b, which may be identical parts in mirror image relation to one another on the axle shaft 28a. A central pinion gear portion 28c is rotationally disposed in the housing portion 18 on or with the axle shaft 28a, and engages a gear rack portion 26a of the injection ram 26. The axle shaft portion 28a may in fact be integral with the pinion gear portion 28c, and the thumbwheel members 28b may thus each include a "gear shaped" recess 28 b' (only one of which is visible in FIG. 3a) formed in each of these thumb wheel parts 28b on one side thereof, which one side confronts the central pinion gear 28c. These recesses receive an end portion of and drivingly engage the pinion gear 28c when the thumbwheel members 28b are assembled onto the axle shaft and are moved axially into engagement with the centralized pinion gear section 28c. Consequently, the thumbwheel members 28b and centralized pinion gear portion 28c are drivingly connected to one another, and rotate in housing portion 18 in unison with one another. Further, each thumbwheel member 28b provides a peripheral tactile engagement surface 28d (i.e., nubbed, ribbed or striated, for example) which is engageable by a thumb of a user of the device 10 to move the injection ram 26, as described above. Thus, this pinion gear assembly provides an effective gear reduction between the thumb of a user of the device 10 and the injection ram 26, so that this ram may be more easily drawn back by rotation of the thumbwheel assembly in order to fill the injection cylinder 14 with medication.

Figure 5:
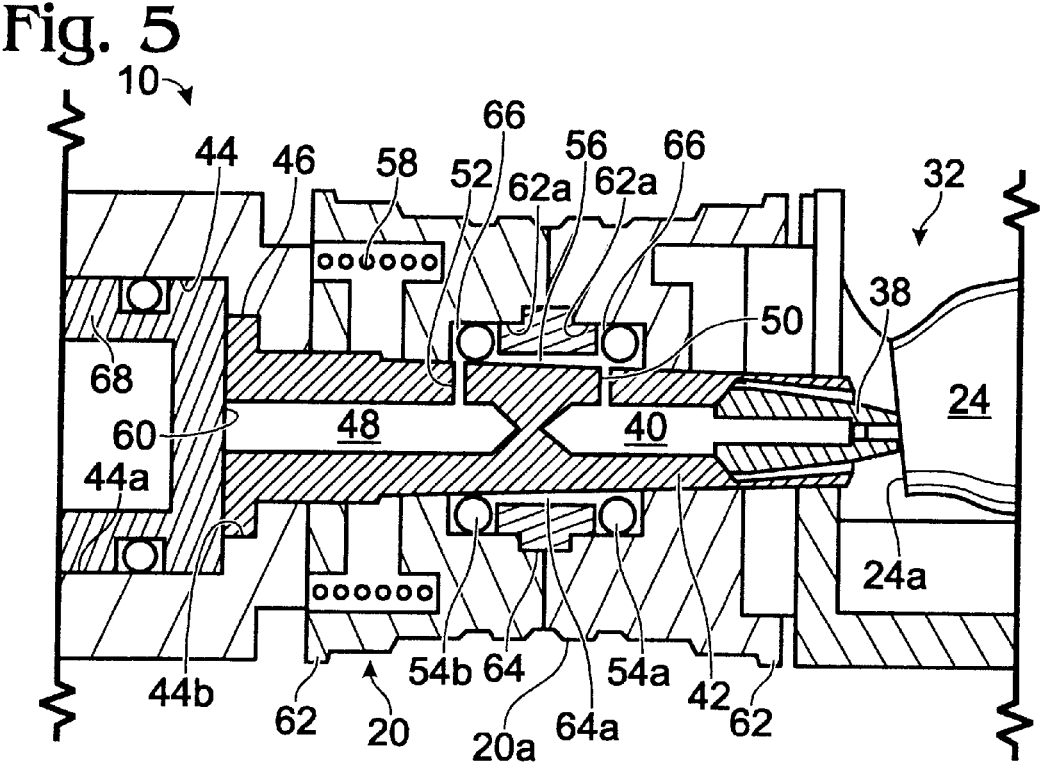
FIGS. 5 and 6 are each enlarged fragmentary cross sectional views similar to enlarged portions of FIGS. 3 and 4, but showing a triggering valve mechanism of the device in respective operative positions, with the position of FIG. 5 being preparatory to a hypodermic jet injection, and the position of FIG. 6 being during such a jet injection.
Figure 6:
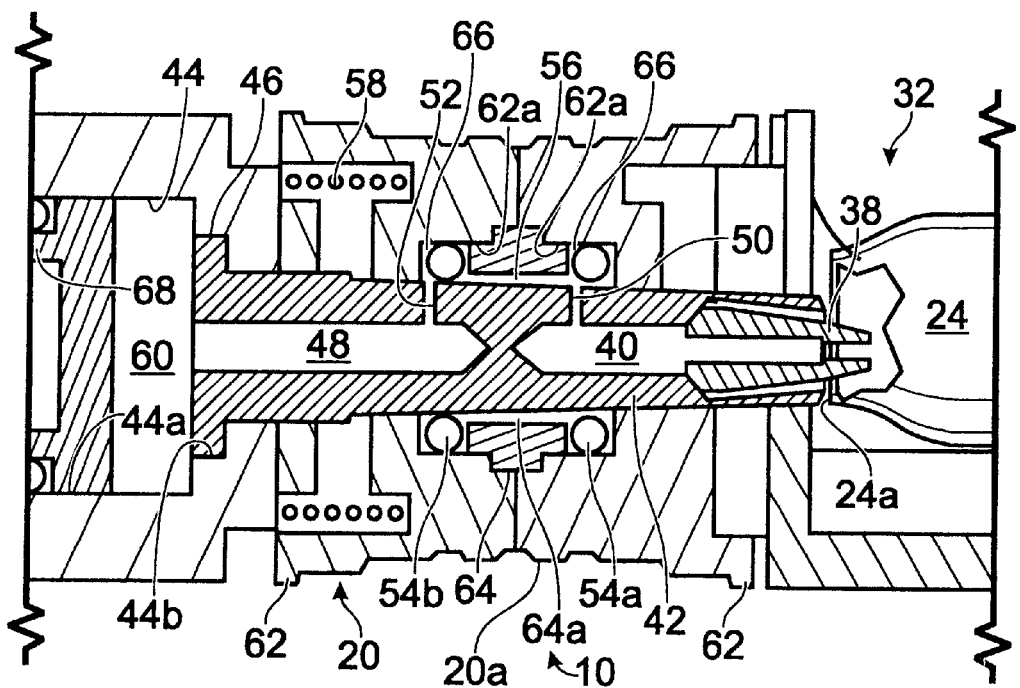

In each of FIGS. 5 and 6 is shown a fragmentary cross sectional portion of the device at the trigger sleeve 20, with the device in a preparatory configuration in FIG. 5 before the beginning of an injection. In FIG. 6, the device is shown during an injection with the trigger sleeve 20 moved forwardly along the stem 42 from its position seen in FIGS. 3, 4 and 5. Viewing first FIG. 5, it is seen that the forward body portion 18 defines a stepped through bore 44 (best seen in FIG. 3) having a larger diameter portion 44a which extends from the forward end (i.e., the left end as seen in FIG. 3) toward the aft end of the body portion 18 and device 10. At the forward end of the body portion 18 this body carries a latching mechanism for receiving and retaining the injection cylinder 14, as explained above. The latching mechanism is releasable to allow removal of the injection cylinder 14 when desired.

An elongate window slot 18a opens from bore portion 44a outwardly on the body portion 18, and is seen in FIG. 1. Particularly, this window slot 18a is seen in FIG. 1 having a volume measurement scale 18b disposed on the body portion 18 adjacent to this window slot 18b. Another slot 18c opens from the bore portion 44a outwardly on the body portion 18 and rotationally accepts the thumb wheel assembly 28. A pointer 26b is carried by the injection ram member 26, and moves in slot 18a and relative to measurement scale 18b to provide to a user of the device 10 an indication of the volume of liquid medication drawn into the injection cylinder 14 by withdrawal of injection piston 16, as was explained above.

Bore portion 44a of the body portion 18 communicates with a second bore portion 44b of slightly smaller diameter, and a head portion 46 is sealingly received in the bore portion 44b, and defines and carries the axially extending stem portion 42 extending rightwardly of the forward body portion 18, to carry the aft body portion 22, and upon which the trigger sleeve 20 is carried. The stem portion 42 defines a second blind bore 48 opening leftwardly, as is seen in FIGS. 3, 4, and 5. The bores 40 and 48 do not communicate with one another inside of the stem portion 42. However, opening radially and outwardly from each bore 40 and 48 adjacent to the blind end of each is one or more fine dimension radial passages 50 and 52. These passages open outwardly on the stem portion 42 at axially spaced apart locations within the trigger sleeve 20. The second blind bore 48 opens leftwardly into the bore portion 44a to the left of the head portion 46, viewing FIGS. 3 and 5.

Viewing FIGS. 3, 5, and 6, it is seen that slidably carried on the stem member 42 is the trigger sleeve 20, which serves as a spool valve relative to interrupting and facilitating communication between the radial passages 50 and 52. According to the illustrated preferred embodiment of the device, the trigger sleeve member 20 carries a pair of axially spaced apart O-ring seal members 54a and 54b. In a first position of the trigger sleeve member (as is seen in FIGS. 3, 4 and 5) the O-rings 54a and 54b bracket the one radial passage 50. Between the O-rings 54a and 54b, an axial gap 56 defined between the stem 42 and sleeve 20 provides a chamber in which pressurized gas from the gas cartridge 24 is captively received in the first position of the trigger sleeve 20. A coil spring 58 extends between the body portion 18 and the trigger sleeve 20 to yieldably bias this trigger sleeve 20 to the first position seen in FIGS. 3, 4 and 5. The trigger sleeve member 20 defines a grooved, knurled, or otherwise textured manual engagement surface 20a.

Further, those ordinarily skilled in the pertinent arts will appreciate that the invention is not limited to having the trigger sleeve member 20 carry O-ring sealing elements, like seal members 54a and 54b. That is, sleeve member 20 may carry a different kind of sealing device or ring, or the sleeve member 20 may itself integrally define a pair of axially spaced apart sealing bands or elements which sealingly and slidably engage the stem member 42.

FIG. 6 shows the device 10 immediately after the trigger sleeve 20 is slid forward by a user of the device to a second position to trigger a hypodermic jet injection as described above. The trigger sleeve 20 slides forward against the bias of the spring 58 and against the friction of the two O-ring seals 54a and 54b to the second position seen in FIG. 6. In this second position for the trigger sleeve, the pair of O-ring seals 54a and 54b bracket the pair of radial passages 50 and 52. That is, the chamber defined at gap 56 now communicates with both radial passages 50 and 52 so that pressurized gas flows from the cartridge 24 through the penetrator 38, along bore 40, radially out passage 50, along axial gap 56 (i.e., in the chamber provided by this gap between the O-rings 54a and 54b) to radial passage 52, and from the radial passage 52 along bore 48 to a variable-volume chamber 60 in the forward body portion 18 within bore 44.

As is seen in FIGS. 5 and 6, the trigger sleeve 20 is composed of two identical mirror image members 62. These members 62 may be substantially identical, and are installed slidably upon the stem 42 in face-to-face relationship so that they have mirror image symmetry. Each of the members 62 defines one of a pair of stepped axial recesses 62a, which recesses are disposed toward one another in the arrangement of the members 62, as is seen best in FIGS. 5 and 6. Disposed sealingly between and in bonding relationship to the members 62 is a sleeve-like central member 64. The central member 64 is received into the stepped recesses 62a, and is shorter than these recesses to cooperatively define a pair of radial grooves 66 receiving the O-rings 54a and 54b. The sleeve member 64 has an axial bore 64a, which is slightly larger in diameter than the stem 42, so as to define the radial gap 56, which is responsible to provide a communication chamber between the O-rings 54a/54b, recalling the description above. The members 62 and member 64 are sealingly bonded to one another, capturing the O-rings 54a/54b in the grooves 66. Because of the configuration of the members 62 and 64, each of these pieces may be injection molded at low cost, and yet provide an easily manufactured spool valve assembly for use in triggering the injection device 10.

Continuing with an explanation of the structure and operation of the device 10, and as will be further explained, the pressurized gas admitted to variable-volume chamber 60 drives a gas piston 68 forcefully forward, driving ram 26 forcefully forward so as to effect a hypodermic jet injection. Importantly, as will be described below, the gas piston 68 and ram 26 are drivingly connected for axial motion in unison by a mechanism which may be termed a "lost motion prevention mechanism," (i.e., a "lost motion preventer") and which mechanism is generally referenced with the numeral 70. This lost motion preventer 70 effectively insures that the variable-volume chamber 60 is substantially at its minimum volume at the beginning of each hypodermic jet injection event, regardless of the axial position of the ram 26 (which axial position is variably dependent upon the volume of liquid medication introduced into the injection cylinder 14), and thus utilizing pressurized gas from cartridge 24 at its highest possible pressure, and preventing or minimizing expansion throttling of pressurized gas from this cartridge as this gas expands into chamber 60. In other words, the lost motion preventer 70 insures that the highest velocity and most forceful hypodermic jet injection is obtained by operation of the device 10 regardless of the volume of liquid medication that is to be injected during any particular injection event.

Further considering now FIGS. 7 and 8, it is seen that the gas piston 68 is movably and sealingly received into the bore portion 44a, and engages against the head 46 of the stem 42 in the minimum-volume position of the chamber 60 for this gas pressure piston. This gas piston member 68 defines a groove 72 in which is carried an O-ring type of sealing member 74. Accordingly, the body portion 18 and gas piston member 68 cooperatively define the variable-volume chamber 60. The gas pressure piston member 68 is cup-shaped, and defines a forwardly opening axial blind bore 76. A forwardly disposed axial end surface 78 of the piston member 68 is slightly angulated from perpendicularity, as is shown to an exaggerated extent in the drawing Figures. An annular clutching member 80 is disposed adjacent to the end surface 78 of the piston member, and defines a bore 82. The bore 82 of clutching member 80 closely (and in a first position of the clutching member 80) slidably receives a cylindrical end portion 26c of the ram 26. The member 80 at bore 82 defines a fine-dimension gap 84 with the ram portion 26c, as is exaggerated in the drawing Figures for ease of illustration.

A small axially extending bore 86 is defined in the gas pressure piston 68, at the circumferential location of this piston where the axial slope of the end surface 78 results in a minimum length for this piston. A small coil compression spring 88 is received in the bore 86, and extends outwardly of this bore in order to urge the clutch member 80 to its first position, as is seen in FIG. 7. In this first position for the clutching member 80, the ram 26 is freely movable in and through the clutch member 80, as a user of the device 10 retracts the ram in order to draw medicine into the injection cylinder 14, for example. A larger coil compression spring 90 extends forwardly from the clutching member 80 to a bushing member 92 received in to the 44a and carrying the ram 26. The spring 90 is effective to urge gas piston 68 rightwardly (viewing the drawing Figures) to a minimum-volume position for the chamber 60, viewing particularly FIG. 7.

Now, it will be understood that when a user of the device 10 triggers a jet injection, high pressure gas admitted to chamber 60 results in a high forward acceleration for the gas piston 68. This high rate of acceleration for the piston 68, in response to a slight axial relative movement between the piston 68 and ram 26, tips the clutching member 80 from its position seen in FIG. 7, to a second position seen in FIG. 8 in opposition to the spring 88. In the second position for the clutching member 80, the annular clutching member 80 is angulated relative to the portion 26c of the ram 26, and bites, jams, or wedges on this ram portion, as is best seen in FIG. 8. Consequently, further forward motion of the piston 68 drives also the ram member 26 forwardly to effect a hypodermic jet injection.

Upon the completion of the jet injection, and when the user opens door 34 and disengages the cartridge 24 from penetrator 38, pressurized gas is controllably vented from the chamber 60, allowing spring 90 to return the gas piston 68 to its first position. During this return movement of the gas piston, the clutching member 80 is in its first position, and simply moves along the portion 26c of the ram 26. Thus, the ram 26 is left in its fully advanced position preparatory to the user refilling the cylinder 14 with a next-subsequent dose of medicine.

Viewing now FIGS. 9–11, an alternative embodiment of a needle-free, jet injection device is shown. This alternative embodiment is the same as the first embodiment described below. Further, because the device illustrated in FIGS. 9–11 has many features that are the same as, or which are analogous in structure or function to those first illustrated and first described above, these features are indicated on FIGS. 9–11 using the same reference numeral used above, and increased by one-hundred (200).

Considering now FIGS. 9–11 in conjunction with one another, it is seen that the alternative embodiment of the jet injector device 210 illustrated by these drawing Figures includes a different configuration of gas piston 268, and a different structure and function of the lost motion preventer 270. The gas pressure piston 268 and ram 226 are drivingly connected for axial motion in unison by the lost motion preventer mechanism 270, as was described above with respect to FIGS. 1–8. However, the lost motion preventer 270 of FIGS. 8–11 depends not on inertia as was the case for mechanism 70, but upon a slight axial relative motion between gas pressure piston 268 and ram 226, as is further described below.

Considering now FIGS. 9–11, it is seen that the gas piston 268 is movably and sealingly received into the bore portion 244a, and engages against the head 246 of the stem 242 in the minimum-volume position of the chamber 260 for this gas pressure piston 268. This gas piston member 268 defines a groove 272 in which is carried an O-ring type of sealing member 274. Accordingly, the body portion 218 and gas piston member 268 cooperatively define the variable-volume chamber 260. The gas pressure piston member 268 is a multi-part, generally cup-shaped assembly, and defines a forwardly opening axial blind bore 276. An end portion 226c of the ram is received into the bore 276. However, the portion 226c is in this embodiment not purely cylindrical, as was the case for the first embodiment described above. Instead, the end portion 226c of ram 226 defines an axially extending array of plural circumferential grooves 94. Each groove 94 is cooperatively defined by a pair of angulated circumferential surfaces 94a and 94b, which intersect to form a generally V-shaped groove (and a corresponding V-shaped ridge, indicated with arrowed numeral 94c). However, the surfaces 94a and 94b do not have equal angulation relative to the axis of the ram 226. That is, the surfaces 94a each define a acute angle relative to the axis or ram 226, while the surfaces 94b each define an obtuse angle to the axis of ram 226. As a result, the portion 226c of ram 226 is provided with an axial array of plural circumferential "teeth" at the plural axially arrayed circumferential ridges 94c defined by the surfaces 94a/94b.

In order to drivingly engage the ridges 94c of the ram 226, gas piston 268 captively receives and carries an internally toothed collet member 96. The collet member 96 may be of the slit type, or may be split into two or more circumferentially extending sub-parts, as will be understood to those ordinarily skilled in the pertinent arts. Alternatively, the collet member 96 may be composed of separate sub-parts, for which movement in unison is insured by a unison ring or joining ring, for example (not illustrated in the drawing Figures). Such a unison ring will also be well understood to those ordinarily skilled in the pertinent arts. Further, although collet member 96 will be seen to include only a single circumferentially extending "jaw" for engagement with a selected one of the grooves 94, the invention is not so limited. That is, the collet member 96 may be provided with plural axially spaced "jaws" or engagement surfaces, each for engaging a respective one of the grooves 94 on ram portion 226c. Further considering the collet member 96, it is seen that this particular embodiment includes a collet 96 having a single radially inwardly extending jaw surface 98 for engaging into a groove of the portion 226c of ram 226, as is perhaps best seen in a second position for the collet member 96 illustrated in FIG. 10.

Considering now FIG. 9, the gas piston 268 and collet 96 are seen in a first position preparatory to a user of the device withdrawing the ram 226 rightwardly as medicine is drawn into injection cylinder 14, recalling the description of the first embodiment above. Thus, the collet 96 is in a first open position, and the ram 226 may move through this collet freely.

In order to move the collet from the first free position seen in FIG. 9 to a second, or gripping position, seen in FIG. 10, the collet member 96 defines a male conical tapered surface 100 disposed rightwardly (i.e., toward the aft end of the device 210). This male conical surface 100 confronts and is engageable with a female conical tapered surface 102 which is formed on a first sub-part 268a of the piston member 268. Thus, in response to leftward (i.e., forward) movement of the gas piston member 268 at the beginning of an injection event (as is illustrated in FIG. 10), the gas piston initially moves leftwardly independently of collet 196 and independently of ram 226. However, this short initial movement brings the surfaces 100 and 102 into engagement with one another, and contracts the collet member to the second or gripping position seen in FIG. 10. In this second or gripping position, the jaw surface 98 of the collet 96 engages into one of the grooves 94 of the ram member 226 at grooved end portion 226c thereof, and drives this ram leftwardly (i.e., forwardly) in unison with the gas piston 268.

Upon the completion of the injection event, and upon a user of the device opening and releasing residual gas pressure from the device 210, the gas piston 268 is moved rightwardly (viewing FIGS. 9–11) to its initial position by a coil spring 290. As is best illustrated in FIG. 11, this rightward movement of gas piston 268 engages a female conical tapered surface 104 of the collet member 96 with a male tapered conical surface 106 defined within a second sub-part 268b of the gas pressure piston 268. The two sub-parts 268a and 268b of the gas pressure piston 268 are united for movement in unison by being mutually threadably engaged with one another, as is illustrated at 268c. Consequently, the collet member 96 is once again expanded to its first free position, as is seen in FIG. 11, and is carried by the gas pressure piston 268 as this gas pressure piston is moved by spring 290 back to its first position in bore 44.

In view of the above, it is to be understood that the lost motion preventer mechanism 270 of this second embodiment of the device may be characterized as a linear ratchet mechanism. That is, the ratchet mechanism drives the ram 226 leftwardly in response to leftward motion of the gas pressure piston, and drivingly engages the ram 226 after a very limited lost motion effective to engage collet member 94 with ram 226. On the other hand, when the gas pressure piston 268 is moved rightwardly by spring 290, the acute taper surface 94a on the ram begins opening the collet so that it does not then grip the ram 226, and male tapered conical surface 106 completes opening of the collet 96 as the gas pressure piston moves rightwardly in response to the action of spring 290.

While the invention has been depicted and described by reference to two particularly preferred embodiments of the invention, such reference does not imply a limitation on the invention, and no such limitation is to be inferred. The invention is capable of considerable variation and alteration in its embodiments without departing from the scope of this invention. Accordingly, the invention is intended to be limited only by the spirit and scope of the appended claims, giving cognizance to equivalents in all respects.

We claim:

1. A gas powered hypodermic jet injection device, said device comprising:

a device body having a forward end; an injection cylinder at the forward end of said device body, and said injection cylinder having a cylinder bore in which an injection piston is sealingly movable to cooperatively define a variable-volume chamber for holding a dose of liquid medication;

said injection cylinder defining a fine-dimension injection orifice in liquid flow communication with said variable-volume chamber to receive and discharge liquid medication as a forceful high velocity jet upon forceful movement of said injection piston in said cylinder;

a power source in said device body for forcefully moving said injection piston in said cylinder in response to communication of gas pressure to a gas pressure piston; said power source including a source of pressurized gas for selective communication with said gas pressure piston;

a trigger assembly for selectively effecting communication of pressurized gas from said source to said gas pressure piston; and a lost motion preventing mechanism selectively drivingly connecting said gas pressure piston to said injection piston;

wherein said lost motion prevention mechanism includes said gas pressure piston defining a bore, an injection ram interfacing at a forward end with said injection piston and adjacent to an aft end portion thereof being received into said bore and being selectively associated with said gas pressure piston, and said lost motion prevention mechanism in a first condition selectively allowing relative axial motion of said gas pressure piston and said injection ram, and also said lost motion prevention mechanism in a second condition selectively coupling said injection ram to said gas pressure piston for axial motion in unison therewith.

2. A gas powered hypodermic jet injection device, said device comprising:

a device body having a forward end; an injection cylinder at the forward end of said device body, and said injection cylinder having a cylinder bore in which an injection piston is sealingly movable to cooperatively define a variable-volume chamber for holding a dose of liquid medication;

said injection cylinder defining a fine-dimension injection orifice in liquid flow communication with said variable-volume chamber to receive and discharge liquid medication as a forceful high velocity jet upon forceful movement of said injection piston in said cylinder;

a power source in said device body for forcefully moving said injection piston in said cylinder in response to communication of gas pressure to a gas pressure piston; said power source including a source of pressurized gas for selective communication with said gas pressure piston;

a trigger assembly for selectively effecting communication of pressurized gas from said source to said gas pressure piston; and a lost motion preventing mechanism selectively drivingly connecting said gas pressure piston to said injection piston;

wherein said lost motion prevention mechanism includes said gas pressure piston defining a bore, an injection ram interfacing at a forward end with said injection piston and adjacent to an aft end portion thereof being received into said bore; a clutching member in a first position allowing said injection ram and said gas pressure piston to move axially independently of one another, and said clutching member in response to a selected event moving to a second position clutching said injection ram and said gas pressure piston for axial movement in unison.

3. The jet injection device of claim 2 wherein said selected event is selected from the group consisting of: rapid acceleration of said gas pressure piston in response to communication of pressurized gas to said gas pressure piston, and relative axial motion of said gas pressure piston and said injection ram in response to communication of pressurized gas to said gas pressure piston.

4. A gas powered hypodermic jet injection device, said device comprising:
   a device body having a forward end; an injection cylinder at the forward end of said device body, and said injection cylinder having a cylinder bore in which an injection piston is sealingly movable to cooperatively define a variable-volume chamber for holding a dose of liquid medication;
   said injection cylinder defining a fine-dimension injection orifice in liquid flow communication with said variable-volume chamber to receive and discharge liquid medication as a forceful high velocity jet upon forceful movement of said injection piston in said cylinder;
   a power source in said device body for forcefully moving said injection piston in said cylinder in response to communication of gas pressure to a gas pressure piston; said power source including a source of pressurized gas for selective communication with said gas pressure piston;
   a trigger assembly for selectively effecting communication of pressurized gas from said source to said gas pressure piston; and
   a lost motion preventing mechanism selectively drivingly connecting said gas pressure piston to said injection piston;
   wherein said trigger assembly includes a trigger sleeve including a pair of substantially identical portions arranged in mirror image relationship to one another, said pair of substantially identical portions each defining an axially extending recess, and the axially extending recesses of each of said pair of substantially identical portions cooperatively defining a blind axially extending recess, said trigger sleeve carrying a pair of seal elements in axially spaced apart relation within said blind axially extending recess, and a central member disposed within said blind recess and between said pair of seal elements and sealingly associating with each of said substantially identical portions, said central portion defining a bore providing an axial flow path for pressurized gas from said source to said gas pressure piston.

5. The jet injection device of claim 4 wherein said injection device includes a stem member slidably carrying said trigger sleeve, and said stem member further defines a pair of axially extending bores aligned with one another and extending from opposite ends of said stem member toward but short of one another but not communicating internally of said stem member, said stem member also defining at least one cross bore extending outwardly from each of said pair of axially extending bores to open outwardly on an outer surface of said stem member there to define a respective one of a pair of ports.

6. The jet injection device of claim 5 wherein in response to sliding motion of said trigger sleeve along said stem between a first position and a second position said pair of seal members move from a respective first orientation in which said pair of seal members straddle a single one of said pair of ports, and to a second orientation in which said pair of seal members straddle both of said pair of ports and pressurized gas communicates within said central member therebetween.

7. A gas powered hypodermic jet injection device, said device comprising:
   a device body having a forward end; an injection cylinder at the forward end of said device body, and said injection cylinder having a cylinder bore in which an injection piston is sealingly movable to cooperatively define a variable-volume chamber for holding a dose of liquid medication;
   said injection cylinder defining a fine-dimension injection orifice in liquid flow communication with said variable-volume chamber to receive and discharge liquid medication as a forceful high velocity jet upon forceful movement of said injection piston in said cylinder;
   a power source in said device body for forcefully moving said injection piston in said cylinder in response to communication of gas pressure to a gas pressure piston; said power source including a source of pressurized gas for selective communication with said gas pressure piston;
   a trigger assembly for selectively effecting communication of pressurized gas from said source to said gas pressure piston; and
   said device body defining an axially elongate recess opening along a side thereof, a door member in a first position closing said recess, and said door member opening to a second position to reveal said recess and a penetrator member disposed within said recess, said recess being sized and configured to accept a pressurized gas capsule including a penetrable diaphragm portion and an end surface opposite to said penetrable diaphragm portion, said door member including a camming surface engaging said end surface, and in response to closing of said door member from said second position to said first position said camming surface moving said pressurized gas capsule fully into said recess and impaling said pressurized gas capsule at said penetrable diaphragm portion upon said penetrator member.

8. A The jet injection device of claim 7 wherein said door member further includes a reentrant portion in said first position of said door closing a portion of said recess, and in said second position of said door member said reentrant portion protruding into said recess to support said gas pressure capsule in a relatively angulated position relative to an axis of said injection device, whereby, after closing of said door member to said second position and penetration of said pressurized gas capsule reopening of said door member to said second position forces said pressurized gas capsule once again to a relatively angulated position relative to said axis of said injection device and partially out of said recess so that said gas capsule is dislodged at said diaphragm portion from said penetrator member.

9. A gas powered hypodermic jet injection device, said device comprising:
   a device body having a forward end; an injection cylinder at the forward end of said device body, and said injection cylinder having a cylinder bore in which an injection piston is sealingly movable to cooperatively define a variable-volume chamber for holding a dose of liquid medication;

said injection cylinder defining a fine-dimension injection orifice in liquid flow communication with said variable-volume chamber to receive and discharge liquid medication as a forceful high velocity jet upon forceful movement of said injection piston in said cylinder;

said injection piston abutting a movable ram member having an elongate gear rack section formed along a side thereof, a thumb wheel rotationally carried by said injection device body, and said thumb wheel including a pair of laterally spaced apart wheel portions each defining a peripheral tactile surface, and a pinion gear member disposed between said pair of wheel portions and drivingly connecting therewith, said pinion gear member drivingly engaging with said gear rack section on said ram member.

10. A method of operating a gas powered hypodermic jet injection device, said method comprising steps of:

providing a device body having a forward end; providing an injection cylinder at the forward end of said device body, and providing said injection cylinder with a cylinder bore in which an injection piston is sealingly movable, utilizing said injection piston and said injection cylinder to cooperatively define a first variable-volume chamber for holding a dose of liquid medication;

providing for said injection cylinder to define a fine-dimension injection orifice in liquid flow communication with said first variable-volume chamber to receive and discharge liquid medication as a forceful high velocity jet upon forceful movement of said injection piston in said injection cylinder;

providing a power source in said device body for forcefully moving said injection piston in said injection cylinder in response to communication of gas pressure to a second variable-volume chamber in which a gas pressure piston is sealingly movable; said power source including a source of pressurized gas for selective communication with said gas pressure piston;

providing a trigger assembly for selectively effecting communication of pressurized gas from said source to said gas pressure piston; and providing a volume minimizing mechanism variably connecting said injection piston and said gas pressure piston so that said second variable-volume chamber defines a minimum volume when pressurized gas begins communication to said gas pressure piston.

11. The method of claim 10 including the step on including in said volume minimization mechanism a clutching member which in response to a limited axial relative movement of said gas pressure piston and said injection piston drivingly engages said injection piston and said gas pressure piston to thereafter move axially in unison.

12. A method of providing a gas powered hypodermic jet injection device, said method comprising steps of:

providing a device body having a forward end; providing an injection cylinder at the forward end of said device body, disposing sealingly in said injection cylinder an injection piston to cooperatively define a variable-volume chamber for holding a dose of liquid medication;

providing said injection cylinder with a fine-dimension injection orifice in liquid flow communication with said variable-volume chamber, and utilizing said injection orifice to receive and discharge liquid medication as a forceful high velocity jet upon forceful movement of said injection piston in said injection cylinder;

providing a power source in said device body for forcefully moving said injection piston in said cylinder in response to communication of gas pressure to a gas pressure piston; providing for said power source to include a source of pressurized gas for selective communication with said gas pressure piston;

providing a trigger assembly for selectively effecting communication of pressurized gas from said source to said gas pressure piston; and configuring said device body to define an axially elongate recess opening along a side thereof, providing a door member in a first position closing said recess and said door member opening to a second position to reveal said recess and a penetrator member disposed within said recess;

providing for said recess to be sized and configured to accept a pressurized gas capsule including a penetrable diaphragm portion and an end surface opposite to said penetrable diaphragm portion;

including on said door member a camming surface engaging said end surface, and in response to closing of said door member from said second position to said first position utilizing said camming surface to move said pressurized gas capsule fully into said recess and to be impaled at said penetrable diaphragm portion upon said penetrator member.

13. The method of claim 12 where in said door member is further provided with a reentrant portion, said reentrant portion in said first position of said door closing a portion of said recess, and utilizing said reentrant portion in said second position of said door member to protrude into said recess to support said gas pressure capsule in a relatively angulated position relative to an axis of said injection device; and after closing of said door member to said second position and penetration of said pressurized gas capsule utilizing said reentrant portion upon reopening of said door member to said second position to force said pressurized gas capsule once again to a relatively angulated position relative to said axis of said injection device, and utilizing said movement of said gas capsule to said relatively angulated position to dislodged said gs capsule at said diaphragm portion from said penetrator member.

14. A method of providing for convenient filling of a gas powered hypodermic jet injection device, said method comprising steps of:

providing said injection device with a device body having a forward end; providing an injection cylinder at the forward end of said device body, and providing for said injection cylinder to define a cylinder bore in which an injection piston is sealingly movable to cooperatively define a variable-volume chamber for holding a dose of liquid medication;

providing for said injection cylinder to define a fine-dimension injection orifice in liquid flow communication with said variable-volume chamber, and utilizing said injection orifice to receive and discharge liquid medication as a forceful high velocity jet upon forceful movement of said injection piston in said cylinder;

providing for said injection piston to abut a movable ram member, and configuring said movable ram member to have an elongate gear rack section formed along a side thereof, providing a thumb wheel rotationally carried by said injection device body; and configuring said thumb wheel to include a pair of laterally spaced apart wheel portions each defining a peripheral tactile surface, and providing a pinion gear member disposed between said pair of wheel portions and drivingly connecting therewith, and drivingly engaging said pinion gear member with said gear rack section on said ram member so that manual rotation of said thumb wheel portions is effective to retract said ram member along with said injection piston within said injection cylinder.

* * * * *